(12) United States Patent
Ralovich et al.

(10) Patent No.: US 10,835,210 B2
(45) Date of Patent: Nov. 17, 2020

(54) THREE-DIMENSIONAL VOLUME OF INTEREST IN ULTRASOUND IMAGING

(71) Applicant: Siemens Medical Solutions USA, Inc., Malvern, PA (US)

(72) Inventors: Kristof Ralovich, Erlangen (DE); Tobias Heimann, Erlangen (DE); Wilko Gerwin Wilkening, Mountain View, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1225 days.

(21) Appl. No.: 14/673,583

(22) Filed: Mar. 30, 2015

(65) Prior Publication Data

US 2016/0287214 A1  Oct. 6, 2016

(51) Int. Cl.
A61B 8/00 (2006.01)
A61B 8/08 (2006.01)
G01S 15/89 (2006.01)
G01S 7/52 (2006.01)

(52) U.S. Cl.
CPC ............ *A61B 8/483* (2013.01); *A61B 8/08* (2013.01); *A61B 8/469* (2013.01); *A61B 8/5215* (2013.01); *G01S 7/52063* (2013.01); *G01S 15/8993* (2013.01); *A61B 8/463* (2013.01); *A61B 8/5207* (2013.01)

(58) Field of Classification Search
CPC ......... A61B 8/483; A61B 8/5215; A61B 8/08; A61B 8/469; A61B 8/5207; A61B 8/463; G01S 7/52063; G01S 15/8993; G06T 7/0012

USPC ....................................................... 600/443
See application file for complete search history.

(56) References Cited

U.S. PATENT DOCUMENTS

| 5,873,830 A | 2/1999 | Hossack et al. |
| 8,894,579 B2 | 11/2014 | Abe et al. |
| 2003/0028107 A1* | 2/2003 | Miller .............. A61B 5/6819 600/437 |

(Continued)

FOREIGN PATENT DOCUMENTS

| CN | 102081697 A | 6/2011 |
| EP | 1685799 | 8/2006 |

(Continued)

OTHER PUBLICATIONS

Kai E. Thomenius, "Evolution of ultrasound beamformers",1996, Proceedings 1996 IEEE Ultrasonics Symposium, pp. 1615-1662, Nov. 03 (Year: 1996).*

(Continued)

*Primary Examiner* — Rochelle D Turchen (57) ABSTRACT

A volume of interest is ultrasonically imaged. An object of interest is automatically located from a volume scan. In one approach, a geometric bounding box surrounding the object is found by a classifier. In another approach, an option for zooming to the object is indicated to the user. A scan region is defined around the object or the bounding box automatically, whether in response to user selection of the option or not. The scan region is shaped based on the ultrasound scan format, but is smaller than the volume. The volume of interest defined by the scan region is used to generate images with a greater temporal and/or spatial resolution than scanning of the entire original volume.

11 Claims, 2 Drawing Sheets

(56) References Cited

U.S. PATENT DOCUMENTS

| | | | |
|---|---|---|---|
| 2005/0096538 A1* | 5/2005 | Chomas | A61B 8/14 600/437 |
| 2005/0228280 A1* | 10/2005 | Ustuner | A61B 8/06 600/443 |
| 2007/0078344 A1* | 4/2007 | Rafter | A61B 8/08 600/450 |
| 2007/0276237 A1* | 11/2007 | Li | G01S 7/52095 600/437 |
| 2008/0072151 A1* | 3/2008 | Song | G06F 3/0481 715/708 |
| 2009/0074280 A1 | 3/2009 | Lu et al. | |
| 2011/0125022 A1* | 5/2011 | Lazebnik | A61B 8/4461 600/444 |
| 2011/0144495 A1* | 6/2011 | Wilkening | A61B 8/0883 600/443 |
| 2011/0213250 A1* | 9/2011 | Vion | A61B 6/032 382/131 |
| 2012/0066241 A1* | 3/2012 | Geller | G06F 19/321 707/758 |
| 2012/0093383 A1* | 4/2012 | Claus | A61B 6/032 382/131 |
| 2013/0018264 A1* | 1/2013 | Gerard | A61B 8/463 600/443 |
| 2014/0052001 A1* | 2/2014 | Ionasec | A61B 8/065 600/441 |
| 2014/0163380 A1* | 6/2014 | Lee | A61B 8/06 600/454 |
| 2014/0187947 A1 | 7/2014 | Hansegard et al. | |
| 2015/0011886 A1* | 1/2015 | Radulescu | A61B 8/085 600/443 |
| 2016/0038121 A1* | 2/2016 | Waechter-Stehle | A61B 8/085 600/443 |
| 2016/0228095 A1* | 8/2016 | Dalal | A61B 8/461 |
| 2016/0262720 A1* | 9/2016 | Henderson | A61B 8/466 |

FOREIGN PATENT DOCUMENTS

| | | |
|---|---|---|
| JP | H10277030 | 10/1998 |
| JP | 2000175914 | 6/2000 |
| JP | 2004275223 | 10/2004 |

OTHER PUBLICATIONS

A. Fenster, D. B. Downey, and H. N. Cardinal, "Three-dimensional ultrasound imaging", 2001, Phys. Med. Biol., vol. 46., pp. R67-R99 (Year: 2001).*

Karadayi et al., "Three-dimensional ultrasound: From acquisition to visualization and from algorithms to systems," 2009, IEEE Reviews in Biomedical Engineering, vol. 2, pp. 23-39 (Year: 2009).*

Prager, U. Z. Ijaz, A. H. Gee and G. M. Treece, "Three-dimensional ultrasound imaging," Feb. 2010, Proceedings of the Institution of Mechanical Engineers, Part H: Journal of Engineering in Medicine, vol. 224, No. 2, pp. 193-223, (Year: 2010).*

J. Powers and F. Kremakau, "Medical ultrasound systems," 2011, Published Online May 18, 2011, Interface Focus, vol. 1, pp. 477-489, (Year: 2010).*

Sofka et al. "Integrated Detection Network (IDN) for Pose and Boundary Estimation in Medical Images," 2011, IEEE International Symposium on Biomedical Imaging: From Nano to Macro, Chicago, IL, USA, pp. 294-299, Published Online Jun. 9, 2011 (Year: 2011).*

Suzuki, "Pixel-based machine learning in medical imaging," 2012, International Journal of Biomedical Imaging, vol. 2012, art. id. No. 792079 (Year: 2012).*

N. Birkbeck, et al., "Fast Boosting Trees for Classification, Pose Detection, and Boundary Detection," Computer Vision and Pattern Recognition Workshops (CVPRW), pp. 36-41, 2011.

Z. Tu, "Probabilistic Boosting-Tree: Learning Discriminative Models for Classification, Recognition and Clustering," Computer Vision (ICCV), vol. 2, pp. 1589-1596, 2005.

* cited by examiner

THREE-DIMENSIONAL VOLUME OF INTEREST IN ULTRASOUND IMAGING

BACKGROUND

The present invention relates to volume imaging in ultrasound. In particular, volume imaging with a region of interest is provided.

Upon scanning a volume of a patient, a smaller volume region of interest is identified. The smaller volume of interest allows for a more targeted usage of the available acquisition time and transducer or system information rate. Higher temporal or spatial resolution is possible by scanning the volume region of interest rather than the entire volume.

In clinical practice, the sonographer is required to manually position the volume of interest. This takes time, so may be less feasible during peri-operative applications (e.g. transesophageal echocardiography (TEE)). Manual updating of the position of the volume of interest relative to the transducer is likewise time consuming. A volume of interest is designated as being at a given position relative to the transducer. Imaging a certain structure continuously with the transducer defined frame of reference may be challenging. It is not easy to hold the transducer steady, and organs may be affected by breathing or heart motion. The transducer or patient motion may cause the structure of interest to move out of the volume of interest, requiring further time consuming manual positioning.

BRIEF SUMMARY

By way of introduction, the preferred embodiments described below include methods and systems for ultrasound imaging of a volume of interest. An object of interest is automatically located from a volume scan. The object may be contiguous or separated into parts. In one approach, a geometric bounding box surrounding the object is found by a classifier. In another approach, an option for zooming to the object is indicated to the user. A scan region is defined around the object or the bounding box automatically, whether in response to user selection of the option or not. The scan region is shaped based on the ultrasound scan format, but is smaller than the volume. The volume of interest defined by the scan region is used to generate images with a greater temporal and/or spatial resolution than scanning of the entire original volume.

In a first aspect, a method is provided for ultrasound imaging of a volume of interest. An ultrasound imaging system acquires data representing a volume of a patient. A processor locates a target bounding box surrounding anatomy of interest and additional anatomy. The processor identifies the volume of interest within the volume as a scan region in a scan format enclosing the target bounding box. The ultrasound imaging system scans the scan region in the scan format. An image is generated from the scanning of the volume of interest.

In a second aspect, a system is provided for ultrasound imaging of a volume of interest. A transducer is connectable with the transmit and receive beamformers. A processor is configured to identify an anatomic structure autonomously from an ultrasonic data set responsive to information from the receive beamformer representing a first region of the patient and is configured to adjust scan parameters to scan just the volume of interest as a sub-part of the first region. The volume of interest includes the anatomic structure. A renderer is configured to generate images only of the volume of interest from scans by the transmit and receive beamformers using the scan parameters. A display is configured to display the images.

In a third aspect, a method is provided for ultrasound imaging of a volume of interest. An ultrasound scanner scans a volume of the patient. A processor locates anatomy in the volume. An option to zoom to the anatomy is presented on a display. The processor identifies the volume of interest as enclosing the anatomy and being less than the volume of the patient. The identifying is in response to user selection of the option. The ultrasound scanner scans the volume of interest and does not scan a rest of the volume of the patient for a plurality of repetitions after the identifying. A sequence of images is generated on a display of the volume of interest. The images are based on ultrasound data responsive to the scanning of the volume of interest.

The present invention is defined by the following claims, and nothing in this section should be taken as limitations on those claims. Further aspects and advantages of the invention are disclosed below in conjunction with the preferred embodiments and may be later claimed independently or in combination.

BRIEF DESCRIPTION OF THE DRAWINGS

The components and the figures are not necessarily to scale, with emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A volume is scanned. For increased temporal and/or spatial imaging of the patient, a volume of interest is defined around an automatically detected object in the volume. The volume of interest is scanned and imaged at the greater temporal resolution, contrast resolution, reduced shadowing, and/or spatial resolution than possible with imaging an entire volume field of view. The volume of interest box is automatically determined from the whole field-of-view three-dimensional image, and subsequently only the focused volume of interest is scanned.

In one embodiment, a machine learning-based object detection controls the image acquisition process. This allows focusing the image acquisition onto the most important regions: where the target anatomy and/or tool are located. The ultrasound beams sample the anatomy sparsely with a full-volume acquisition to locate the object. This location controls the image acquisition process. The ultrasound system automatically recognizes certain structures and optimizes the field-of-view and other imaging parameters. A series of spatially smaller volume of interest acquisitions are performed for the targeted area. Using the fixed transducer bandwidth budget, this allocation scheme allows higher image quality (e.g., increasing temporal and spatial resolution) in the volume of interest as compared to the full-volume.

In another embodiment, an ultrasound system identifies certain structure autonomously in ultrasonic data sets in real-time and adjusts imaging parameters in real-time in order to optimize image quality and to gather data for the anatomic structure. For example, data for the aortic valve over two consecutive heart cycles is gathered after locating the valve from a whole heart scan. As another example, the location of a biopsy needle relative to a pre-defined structure, such as a suspicious lesion, is located.

The volume of interest is anchored dynamically to a target. By repeating sparse temporal and/or spatial scanning of the volume and detection of the anatomy, the regularly placed volume of interest may be imaged in an on-going manner despite patient and/or transducer movement. The ultrasound system adjusts the field of view over time and in a predictive manner to ensure that the structure does not leave the volume of interest. This includes probing adjacent areas in occasional sparse acquisition.

Figure 1:
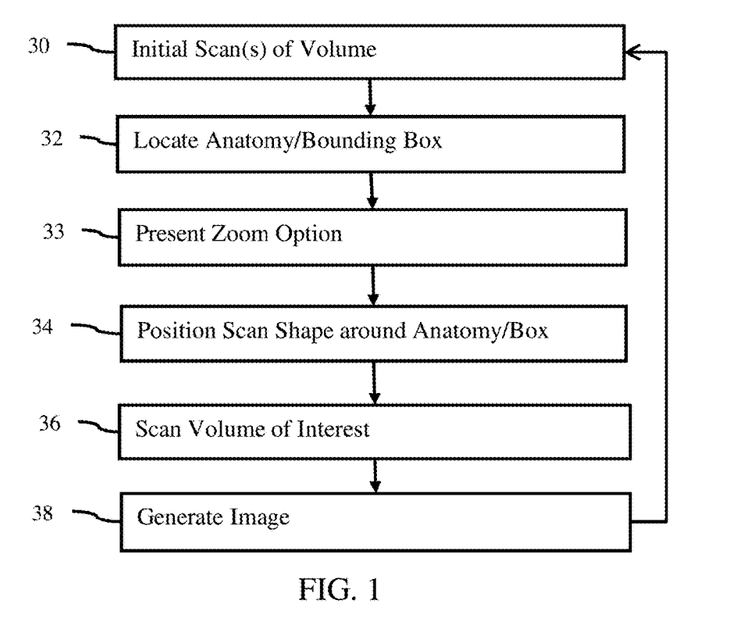
FIG. 1 is a flow chart diagram of one embodiment of a method for ultrasound imaging of a volume of interest.

FIG. 1 shows one embodiment of a method for ultrasound imaging of a volume of interest. In general, an object of interest is detected automatically from a volume scan during three-dimensional ultrasound imaging. The detection may include a bounding box, which is a geometric structure different than the object and not specifically represented in the scan data. A region or volume of interest is defined as a sub-volume around the detected object or bounding box. The volume of interest is scanned multiple times without scans of the volume. The volume of interest is imaged at a greater spatial and/or temporal resolution than possible by scanning the volume. By repeating the detection of the object from a full volume scan with repetitions of the volume of interest scanning, the object location is updated, providing automatic volume of interest imaging oriented at the object of interest.

Figure 4:
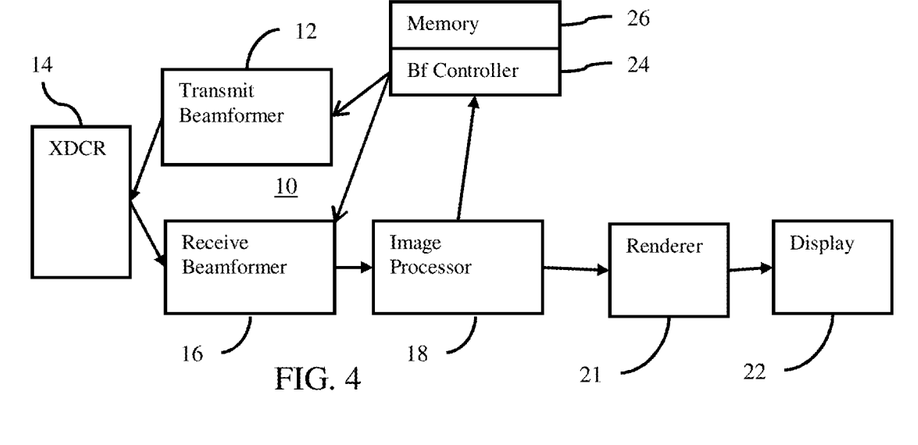
FIG. 4 is a block diagram of one embodiment of a system for ultrasound imaging of a volume of interest.

The method is performed by the system shown in FIG. 4 or a different system. For example, a medical diagnostic ultrasound imaging system scans in acts 30 and 36, and a processor locates in acts 32, presents a zoom option in act 33, and positions a scan shape in act 34. The imaging system generates the displayed image in act 38. Other devices may perform any of the acts, such as the processor performing all of the non-scan acts.

The acts are performed in the order shown or another order. For example, act 33 is performed before acts 32.

Additional, different or fewer acts may be used. For example, act 33 is not performed. As another example, act 32 is not performed and the scan shape is positioned over the detected object rather than a bounding box. In yet another example, the repetition loop from act 38 to act 30 is not performed.

In act 30, data representing a volume of a patient is acquired. The data is acquired with an ultrasound imaging system. The ultrasound imaging scanner scans a volume of the patient. Alternatively, the data is acquired from a previous scan, such as by transfer from a memory or picture archiving and communications system.

A volume of a patient is scanned. This scan is an initial scan, such as a first scan. The initial scan may be the one occurring initially or before anatomy is detected in act 32, even if other previous scans occur before the initial scan. For example, the scanning of act 30 is repeated as a sonographer positions the transducer to scan the desired volume. Once the object of interest is in the field of view, the detection of act 32 occurs, making the volume scan used for the first detection the initial scan for the remainder of the process.

The initial scan is of an entire volume. The entire volume is a field of view established by the scanning. The lateral extent and depth define the extent of the scanned volume. Based on different settings, different size volumes may make up the entire scan volume. The user or the system determines the field of view and resulting entire scan volume in configuring for the initial scan.

To scan a field of view with ultrasound, transmit and receive beams are formed by an ultrasound system. Any scan format, such as sector, linear, or Vector®, and corresponding field of view may be used. The scanning is of a three-dimensional region or a volume. The scan lines are distributed by electric and/or mechanical steering in three-dimensions, providing data representing a volume (e.g., volume of N×M×R voxels, where N, M, and R are integers greater than 1). Any three-dimensional format may be used, such as scanning sequentially along planes such that the scan planes together represent the volume. The scan format or arrangement of scan lines defines a scan region. For example, a linear scan provides a rectangular box scan region. A sector or Vector® scan provides a fan shaped (e.g., cone, truncated cone, pyramid, or truncated pyramid) scan region.

The transmit and/or receive beam characteristics may be set or responsive to values of parameters. The depth and/or lateral extent of the field of view is set. Similarly, the transmit beam focal depth, transmit frequency, receive frequency, line density, sampling density (sampling spacing along a scan line), transmit waveform (e.g., number of cycles and/or envelope shape), frame rate, aperture, and/or other scanning characteristics are set. The number of transmit focal positions per scan line (e.g., one or two) may be set. Different, additional, or fewer scan (e.g., transmit and/or receive) parameters may be used.

Through receive beamformation, the responsive data represents samples in the field of view. Data received from the scanning is detected. A B-mode detector determines the intensity of acoustic echoes represented by the received data. For example, the receive data is formatted as in-phase and quadrature data. A square root of a sum of the squares of the in-phase and quadrature terms is calculated as the intensity. Other measures of the magnitude of the acoustic echo may be used for B-mode detection.

Other B-mode processing may be performed. For example, the detected B-mode data is spatially filtered. As another example, a sequence of frames from a corresponding sequence of scans of the entire field of view is acquired. Different pairs or other sized groupings of the resulting B-mode frames of data are temporally filtered. Infinite impulse or finite impulse response filtering may be used. In another example, a general or overall gain is applied. One or more parameters may establish the overall gain. Additionally or alternatively, depth dependent gains may be applied. Different, additional, or fewer B-mode processing parameters may be used.

In other embodiments, other types of detection and corresponding scans are performed. For example, color flow (e.g., Doppler) estimation is used. Velocity, power, and/or variance are estimated. As another example, harmonic mode is used, such as imaging at a second harmonic of a fundamental transmit frequency. Combinations of modes may be used.

After processing, the detected data is scan converted, if needed. A two-dimensional image may be generated. By creating B-mode images for different planes, display values for a volume are provided. A B-mode image represents the intensity or strength of return of acoustic echoes in the B-mode field of view. The intensities or B-mode data are mapped to gray scale within the dynamic range of the display. The gray scale may be equal or similar red, green, blue (RGB) values used by the display to control pixels. Any color or gray scale mapping may be used.

Data used for other acts is from any point in the processing path. In one embodiment, detected and scan converted scalar values are used prior to any color or display mapping. In other embodiments, beamformed samples prior to detection, detected data before scan conversion, or display values after display mapping are used. The data is in the polar coordinate system used for scanning or is interpolated to a regular grid, such as a Cartesian coordinate system.

The values of the parameters for scanning are initially set using any process. In one embodiment, one or more of the parameters are set based on input by the user, predetermined values, and/or selection of an application or configuration. For example, the user selects volume or three-dimensional imaging of a particular anatomy, such as a heart valve. In alternative or additional embodiments, one or more of the parameters are set based on feedback or adapting to the data received from the scanning. Automatic setting of the value or values of the parameter or parameters is performed. For example, the overall gain and/or dynamic range of B-mode data is set based on identifying B-mode data for locations associated with tissue in the field of view and using an average, median or other B-mode intensity for the tissue locations to set the gain and/or dynamic range.

The values of the parameters may also be initially set for desired imaging quality enhancements. The values for the volume of interest are set through presets. Multiple types of anatomy and image enhancements for different exam types may be available for selection. The user selects the volume imaging application for specific anatomy. The values for the scan settings for the volume and for the volume of interest are pre-determined and used based on the selection of the application. The size (e.g., lateral and/or range extent), orientation, and/or position of the volume of interest may be used to calculate the values of at least some of the scan parameters.

The user may alter or change any of the values for the volume and/or volume of interest scan. In additional or alternative embodiments, one or more of the parameters may be set based on user input or adjustment. For example, the user inputs a minimum desired frame rate of the volume of interest.

During live or real-time imaging (scanning and outputting images at the same time or while the patient has a transducer placed against them), no special interaction is generally required or expected of the user for the targeted volume of interest. The user may select only an application (e.g., three-dimensional imaging of a valve) and the remaining configuration automatically occurs. The user may pre-configure any one or more of the settings and then the imaging occurs without further change by the user. In other embodiments, configurability of the volume of interest and/or volume imaging is still available during the live imaging. The user may alter one or more values of scan parameters without being required or expected to alter as part of the normal workflow.

The initial scan or scans of the entire volume are performed prior to separate scans of the volume of interest. The scanning is configured to cease scans of the volume of the patient while repeatedly scanning the volume of interest multiple times in a given acquisition cycle. The entire sequence of full volume scanning, then ceasing the full volume scanning while scanning the volume of interest may be repeated occasionally or periodically in order to continually position the volume of interest to account for motion. The scanning includes this programmed acquisition cycle.

In act 32, a processor detects an object from the data of the initial scan. The data representing the volume of the patient is processed to detect the object of interest. For example, the user translates and/or rotates the field of view (i.e., moves the transducer) relative to the patient as desired. Once the object is in the field of view, the processor detects the object. For example, a valve is automatically detected from B-mode data representing a volume including at least a portion of a heart.

The detection is automatic during the live imaging. Rather than requiring user input of a location or locations for the object, the processor applies filtering, edge detection, pattern matching, model matching, or other computer assisted classification to detect the object in the data. The processor detects without user input of a location or locations. Multiple variations of scanning techniques may be attempted to identify lesions. Examples are steered spatial compounding and rotation of the scan grid and combinations thereof to aid the detection of cysts. The system may also perform a sparse scan of the full volume first to identify landmarks.

In one embodiment, a machine-learnt classifier is applied by a processor (e.g., central processing unit or graphics processing unit). Haar, gradient, directional, steerable, or other features are calculated from the volume data and input to the machine-learnt classifier. The machine-learnt classifier, based on learning from training data with known truth distinguishing the object of interest from other tissue, fluid or devices, indicates whether the object is represented by the data for the volume and where.

Any machine learning may be used, such as a probabilistic boosting tree, Bayesian network, neural network, or support vector machine. Any feature or feature set may be used. In one embodiment, probabilistic boosting trees with marginal space learning train a classifier based on Haar and steerable features. In another embodiment, a random forest regression is used to train.

A feedback may be provided. The feedback indicates correctness of located objects. This feedback may be used as additional training data to re-learn or improve the machine-learnt classifier. An online-learning-based tracking is possible, where selection of a target area requires a single iteration. Online-learning may include online random forest, online bagging, or sparse online learning. In case a trained classifier (or regressor) outputs a candidate box which is off compared to or not located where the user expects the box, then the user draws a box on a full volume image where the box should be positioned. This location is then forwarded to the online learning, which will subsequently track the object correctly by relearning, based at least in part, on the returned volume and corrected box location as training data.

The object to be located is any object, such as anatomy or a device. For example, a valve is located. A specific valve may be located. The atrial valve annulus ring, aortic root, left ventricular outflow tract, parts of liver, or other anatomic locations or lesions may be located. In other embodiments, devices, such as surgical instruments or implants (e.g., catheter, tool shaft, needle, or surgical device such as a prosthetic annulus or valve), are detected instead of anatomy. Anatomy and added devices may both be detected in a given volume. Different or the same detector detects the different anatomy and/or devices. The object is any anatomic region, catheter (e.g., lasso), or tool that machine learnt or other detectors detect.

The detected anatomy or device has any spatial extent. For example, the anatomy extends by multiple voxels in one or more dimensions. The anatomy has any shape, such as a smoothly varying curved shape. Jagged or flat portions may occur. A device may have a smooth surface.

The detection provides a location of the object of interest. Features, surfaces, and/or interior portions of the object are found. Features represented by the data but not belonging to the object of interest may be used to locate the object of interest. Voxels representing the anatomy are labeled or flagged as belonging to the anatomy. The detection determines whether or not the object is represented by the data. The detection determines where, if represented, the object is represented.

Due to motion, voxels that are part of the object at one moment may not be part of the object at another moment. To allow for some motion, more than the object may be located. For example, a margin of a certain distance or number of voxels around the object is located. In one embodiment, a bounding box is located. The detection is not of the object alone, but of the object and a location of a bounding box to enclose the object. Different parts of the object may move by different amounts, so the bounding box is sized and/or oriented to account for the variations.

While the data does not represent a bounding box, the bounding box is positioned based on the object represented by the data and/or other features represented by the data. In one embodiment, a machine-learnt classifier locates the bounding box. Experts annotate training data with bounding boxes. The machine training then learns the position of the bounding box based on the ground truth in the training data representing scans of patients. The machine learns to position the bounding box given data representing the patient. The processor locates the bounding box using the matrix or matrices of the machine-learnt classifier. The distinguishing features used to locate the bounding box may be other than features of the object of interest.

Other detectors or processes may be used. For example, the bounding box is centered at a center of detected anatomy or a feature of anatomy is used to place the bounding box. Orientation may be set based on detected anatomy. Scale may be based on the scale of the anatomy and any desired minimum margin.

The bounding box is any geometric structure. For example, the bounding box is a cuboid of six sides joined at right angles. As another example, the bounding box has twelve or fewer sides. The shape of the bounding box is different than the organic shape of the anatomy, but generally fits the anatomy. The shape of the bounding box is different or the same as a shape of an inserted object, such as a cylinder bounding box enclosing a needle or catheter tip.

The bounding box is sized and oriented to enclose the object of interest. Since the shape, orientation, and/or scale are different than the object, the bounding box encloses more than the object of interest. One or more (e.g., many) voxels not representing the object are included in the bounding box with the voxels representing the object. In alternative embodiments, the bounding box fits to the object and does not enclose voxels not belonging to the object.

Figure 2A:
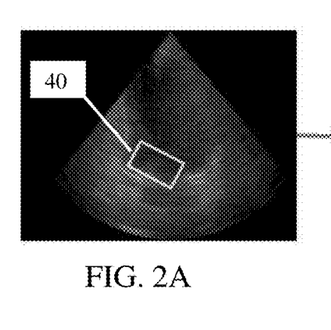
FIGS. 2A-C illustrate examples of a bounding box, scan region, and zoomed display, respectively.

The detection determines a position, orientation, and size of the target bounding box to encompass the object of interest. The target bounding box is parameterized by position (x,y,z), 3D orientation ($\alpha,\beta,\gamma$) and size ($s_x$, $s_y$, $s_z$). FIG. 2A shows an example. An intersection of a bounding box 40 different in size and shape from the enclosed object is shown positioned in a cross-sectional image. The localized bounding box extends in three dimensions to enclose the object, but may have one or more open sides. Once the machine-learnt detector localizes the target bounding box, these parameters are used to define the volume of interest in act 34.

In act 33, the processor or imaging system presents an option to the user. The option indicates detection and/or location of the object or bounding box. The user is provided an indication that zooming to the volume of interest is available. The option indicates that the volume of interest may be imaged instead of the full volume.

The option is displayed on a display. For example, the bounding box is displayed as a graphic overlay in an image, such as shown in FIG. 2A. The option is displayed on or over a two-dimensional image or a three-dimensional rendering. An annotation is provided with the graphic overlay. The annotation indicates the availability of zooming to the volume of interest. Other graphics or option presentations may be provided, such as displaying text indicating detection and availability of zooming. The option indicates to the user on the display that an object has been detected. Alternatively, the option solicits whether detection should be performed.

The option provided to the user is selectable, such as with a mouse or trackball and activation key. By the user selecting the option, the processor receives an indication from the user of a desire to zoom to or image just the volume of interest with the object rather than the entire volume. In other embodiments, a hard key, soft key or other user input is provided to zoom instead of or in addition to any graphic display of the option. By activating the key, the user selects.

In one workflow example, the user selects a valve imaging application. The heart volume is scanned and images are rendered in real time. The imaging system detects and locates the valve. More than one valve may be located. The imaging system indicates that the valve or valves have been detected and offers the option to zoom to the valves. The user selects the option for one or more of the valves to transition to imaging of the volume of interest (e.g., volume around the valve). The identification of a scan region and scanning are performed in response to receiving the user selection of the option.

In an alternative workflow, the display and selection of the option to zoom are not provided. The zoom operation or transition to volume imaging of the volume of interest instead of the full volume occurs automatically. The imaging system detects the location of the valve, so transitions to imaging of the volume of interest automatically without user selection of an option during the imaging. Instead of presenting the user with an option for scanning a volume of interest, the system autonomously acquire a volume of interest so that the user only has to review the acquisitions.

In another alternative, the system helps the user position the transducer so that a volume of interest is acquired with better quality. For example, a volume of interest is close to the edges of the full volume where the spatial resolution is sub-optimal. Another example is that the system could identify shadowing or poor acoustic contact. The object is highlighted to the user with a request to reposition the transducer relative to the patient.

In act 34, the volume of interest is identified. While the ultrasound imaging system may scan just in the bounding box or just the object locations, such scanning may waste resources. Without detracting much from spatial and/or temporal resolution, a larger region may be scanned based on the scan format used for scanning. To sample the object and/or the bounding box, scan lines at a given lateral extent are used. Sampling along a greater range of depths than needed detracts little from temporal or spatial resolution. The volume of interest is the scan region instead of the bounding box or object.

The processor identifies the volume of interest as a scan region. The scan region is shaped based on the scan line distribution. For linear scans, the scan lines are parallel. The resulting three-dimensional scan region is a cuboid or rectangular box, but a cylinder shape or other shape may be used. For sector or Vector® scans, the scan lines diverge from a point on the transducer face or a virtual point positioned behind the transducer, respectively. The sector and Vector® scan formats of scan lines scan in a fan or cone shaped region. The Vector® scan may be a fan shaped region without the origin point included, such as resembling a trapezoid in cross section (e.g., truncated cone or truncated pyramid). Other shapes of scan regions may be used, such as a shape formed by a linear, sector, or Vector® sweep by translation and/or rotation of the transducer.

The volume of interest is identified as a scan region sized and/or oriented to the bounding box or object. The scan region is defined to scan the target bounding box or object. By enclosing the bounding box or object in the scan region extent, the object will be scanned.

The scan region is less than the entire volume scanned to locate the bounding box or object. In one embodiment, the scan region is sized to be as small as possible (e.g., laterally and/or in depth) while still including all of the bounding box or object. For example, the volume of interest is automatically calculated as a three-dimensional fan geometry as small as possible while still covering the entire bounding box and having a regular scan geometry. The scan geometry is fit to enclose the bounding box or object without altering the shape of the scan geometry. The scan format that is used for the volume of interest may differ from the scan format that is used for the full volume in order to optimize aspects of image quality and resolution within the volume of interest. The same format may be used.

Figure 2B:
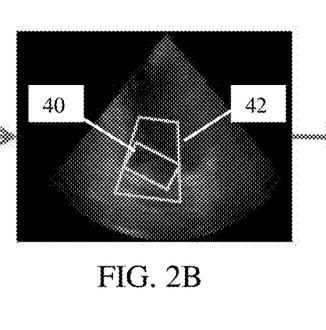

As an alternative to minimization of the scan region about the bounding box or object, a margin may be included. The scan region is identified to have a margin with the bounding box or object so that the bounding box or object is no closer than a given distance from the edge or surface of the scan region. FIG. 2B shows an example. The Vector® scan region 42 is fit to the bounding box 40 at least for the lateral extent. The lateral extent is minimized to be as small as possible while still covering the bounding box in azimuth and elevation. For range or depth, a margin is provided. The margin is different for the near field than the far field. Any margin may be used.

In one embodiment, the scan region as the volume of interest has boundaries covering the target bounding box in depth, elevation, and azimuth. The volume of interest is a fan shaped 3D region described in the three-dimensional ultrasound cone by the distance of near and far ends ($R_1$, $R_2$) and azimuthal ($Az_{Start}$, $Az_{End}$) and elevation ($El_{Start}$, $El_{End}$) polar spans. The scan format uses a polar coordinate system. The volume of interest is anchored such that the volume of interest completely encloses the bounding box dimensions. Optionally, a margin is applied to preserve more ultrasound image context around the target.

The volume of interest extends over three dimensions. The volume of interest is within the volume, such as being entirely within or being within but having a common edge. The volume of interest may be less than ½, less than ⅓, less than ¼, or have another size ratio relative to the full volume.

The volume of interest is positioned around the bounding box or object as an initial assignment. Since the transducer and/or the object of interest may move relative to the patient, the volume of interest may be sized to cover any movement and/or may be altered in position to account for motion. To optimize frame rate and/or image quality enhancement for the volume of interest, the size is smaller than needed to account for likely movement. After the initial assignment, other assignments may occur to reposition the volume of interest.

By identifying the volume of interest as the scan region enclosing the bounding box or object but less than the entire field of view for the volume scan, the resulting image does not include the full volume, but just the volume of interest. Since a smaller region is scanned, the acquisition may have a higher spatial and/or temporal resolution than for the full volume.

In act 36, the ultrasound imaging system scans the scan region. The ultrasound scanner scans the volume of interest and not the rest of the larger volume. The remaining parts of the full volume outside the scan region 42 are not scanned for any number of repetitions of the scanning of the volume of interest. For example, the volume of interest is scanned four, eight, ten, or more times before scanning the full volume. The ultrasound imaging system performs separate scans for the volume of interest without scanning the entire volume. Different transmission and responsive receive events occur for the volume of interest scan than for the full volume scan.

Since the full volume is less frequently scanned, the temporal resolution of the volume of interest is relatively higher. Since the volume of interest is smaller, less time is needed to complete each scan. As a result, even greater temporal resolution may be provided.

The spatial savings resulting from scanning the smaller volume of interest acquisition window may be traded off for higher spatial resolution in the space of the volume of interest. The physical limits to the spatial resolution are set by the aperture (size) of the transducer and the ultrasound frequency. The scan line density and/or sample density along each scan line may be greater than the scan line density and/or sample density used to scan the full volume. Signal to noise ratio and/or contrast resolution may be improved by scanning the smaller volume instead of the full volume.

The volume of interest is scanned with different values for scan settings than for the scanning of the full volume in act 30. The volume is scanned with scan settings having the different values than for the volume of interest. Any one or more (e.g., two or more) parameters have different values. For example, the line density, transmit power, frame-rate, line (scan) orientation, scan format, and/or transmit focus are different for the volume of interest scan than for the volume scan. In one embodiment, the volume of interest is scanned to provide a greater frame rate, resolution, contrast, or combinations thereof as compared to the larger volume. For example, the line density is greater for the volume of interest than for the full volume.

In the valve example, the scan settings for the volume of interest scan are optimized for valve imaging, such as having a greater frame rate than the full volume. The frame rate may be more important than resolution or contrast, so may be set higher with a sacrifice in spatial resolution and/or contrast. The spatial resolution and/or contrast for the volume of interest may be the same, better, or worse than for the volume. The focus points may be centered in the volume of interest for better focus as compared to using the full volume scan. The transmit energy for the volume of interest may be higher than for the volume. The values are set for the anatomy of interest, so may be set relative to each other for the volume of interest and relative to the full volume. Scanning other anatomy may use the same or different tradeoffs.

In act 38, the data from the scanning of act 36 is used to generate an image. The processor, renderer, or other device generates an image from the volume of interest data. For example, the data from the scanning of the volume of interest is passed to a three-dimensional renderer.

Figure 2C:
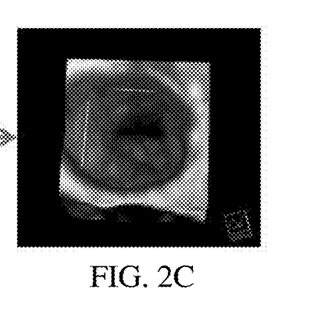

The volume of interest is rendered to an image representing the object. Only the volume of interest is rendered. For each repetition of the scanning in act 36, an image is generated in act 38. The image represents just the volume of interest and not the remaining parts of the full volume. For example, FIG. 2C shows a three-dimensional rendering of the volume of interest without any imaging of the remainder of the full volume shown in FIG. 2B.

In alternative embodiments, the volume of interest and volume may be rendered and displayed separately. Two different images are displayed adjacent to each other. In another embodiment, the volume of interest is rendered and a resulting image is overlaid on a rendering from the volume. The same viewing perspective, but different rendering (e.g., transfer function, type of rendering, color mapping, transparency, or shading) is used for both renderings. The anatomy may be specially marked in the display through luminosity, color, graphic frames, or other visible indicators. In yet another embodiment, the volume of interest data is processed differently, such as by a different transfer function, but then combined with the volume data. The resulting blended data is rendered as an image. Samples from the volume of interest and the other parts are temporally and spatially blended so that the image represents the entire volume.

A sequence of images of the volume of interest is generated. As the scanning is repeated, corresponding image generation is also repeated. Each newly acquired set of data representing the volume of interest is used to generate an image. Live imaging updated as the data becomes available is performed. The images are generated at the same frame rate as the volume of interest scan.

The three-dimensional images are generated with rendering. Any rendering may be used, such as projection or surface rendering. Shading may or may not be added. In other embodiments, a multi-planar reconstruction or other imaging format from a data set representing three dimensions is used.

The images are B-mode images, but may be other modes. The image is generated without a graphic showing the object or bounding box. Alternatively, a graphic or other difference indicates the object and/or bounding box.

The imaging is used for diagnosis and/or treatment guidance. Enhanced imaging of valves may assist in interventional cardiology and structural heart diseases. The volume of interest is shown with a temporal or spatial resolution not otherwise available when scanning the larger volume. Enhanced images of an inserted object may be used to guide the insertion, positioning, and/or use.

If frame rates permit, more than one volume of interest may be used within the same large volume. The location of the object in act 32, positioning of the scan shape in act 34, scanning of the volume of interest in act 36, and/or generating of the image in act 38 are performed for each of the objects of interest, resulting in two images for the two objects.

A feedback loop is shown from act 38 to act 30. Since the object may move relative to the transducer over time, the process is repeated. The bounding box and/or volume of interest sizing may account for some or all of the likely movement, so repetition of act 30 may not be needed. To optimize the imaging (e.g., enhanced resolution and/or contrast) and/or deal with unexpected movement, the sizing of the scan region may be smaller but with feedback. The full volume is scanned again in act 30 to locate the object or bounding box in act 32 again. This location may be different or the same. The zoom option presentation in act 33 may not be repeated since the selection of the option was previously provided. The scan shape is positioned in act 34 for any new location of the object and/or bounding box. The scanning in act 36 and resulting image generation of act 38 are repeated.

Figure 3:
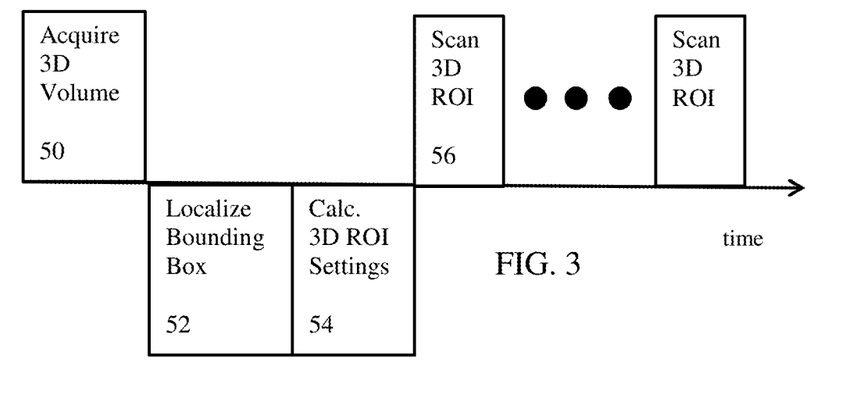
FIG. 3 illustrates an example acquisition cycle.

FIG. 3 shows an example of the acquisition cycle. At act 50, a dense three-dimensional image is acquired. The image is from a scan that includes the object of interest in the ultrasound cone. In act 52, a three-dimensional target bounding box is localized in the volume or three-dimensional ultrasound image. In act 54, the volume of interest acquisition geometry is derived to enclose the three-dimensional bounding box. In act 56, three-dimensional scans and resulting images of the volume of interest are acquired for the rest of the acquisition cycle.

Referring again to FIG. 1, the acts 30, 32, 34, 36, and 38 represent the acquisition cycle. Within the acquisition cycle, one or more images of the volume of interest are generated. For example, four or more images are generated in real-time from a corresponding sequence of four or more scans. The acquisition cycle is timed to limit movement of the object. The object moves at a given rate. The number of repetitions of the scanning and imaging in acts 36 and 38 may be based on the magnitude and/or direction of the movement. The time period of the acquisition cycle is set to a period where the movement of the object is likely to remain in the bounding box or volume of interest. The duration of the acquisition cycle is determined based on anatomic information (e.g. cardiac or respiratory cycle) being imaged. Synchronization between the acquisition cycle and the cardiac cycle may be used to adaptively determine the duration of the acquisition cycle (e.g., use ECG gating). Alternatively, the time period is predetermined or set by the user.

The acquisition cycle is repeated. The initial scanning in act 30 and locating in act 32 are repeated to track the object of interest. Each repetition determines a new location for the object in the volume of the patient. By updating the location periodically, the object is tracked over time. The duration of the acquisition cycle determines the accuracy of the volume of interest placement. In each acquisition cycle, a single or sequence of full-volume scan data is acquired. This data is used to determine the current pose (e.g., position, orientation, and scale) of the volume of interest. In the rest of the acquisition cycle, the volume of interest parameters stay the same (e.g., stationary or fixed in the transducer coordinate system).

The tracking is performed without user input of an indication of the position of the object. The processor performs the detection without user identification of a location of the object. Alternatively, the user inputs an anatomy location.

The tracking may be predictive. Since the motion of the object may be continuous or regular, the location of the object may shift from the time of detection in act 32 to the time the volume of interest is scanned in act 36. The delay may result in the object being at a different location. Similarly, the delay from scan to scan in repetition of act 36 may result in the object being at a different location. This inaccuracy may be acceptable given a margin in the volume of interest. Alternatively, the processor predicts the next location. The motion from one or more previous acquired data sets of the full volume is used to predict the next location for when the next scan is to occur. If the object is moving at a given rate and direction, the rate and direction are used to predict the location by the time the next scan of the volume of interest is to occur. A history of motion, such as associated with cyclical motion, may be used in the prediction. The current phase is used to determine an expected rate and direction for the subsequent scan. The prediction compensates for the lag between scans of the volume of interest and/or of the full volume for updating the location.

The feedback arrow from act 38 to act 30 represents on-going or continuous scanning. The scanning is repeated with the altered location of the volume of interest based on repeated detection of the object. This process continues over time in the live or real-time imaging, tracking the object in the volume. The object of interest continues to benefit from greater frame rate, resolution, and/or contrast (i.e., image quality) over time despite movement. By tracking automatically, the volume of interest may be made smaller, allowing for more optimized imaging of the anatomy.

By automatically detecting and tracking by updated detection of the object, three-dimensional imaging may be performed without the user having to adjust imaging parameters, such as for the volume of interest size and position. The detection, such as with a machine-learnt classifier, increases the speed of operation of the imaging system to allow for real-time detection. The reliability of measurements based on the volume of interest is increased by ensuring that landmarks are included and that the image quality is optimal.

FIG. 4 shows one embodiment of a system 10 for ultrasound imaging of a volume of interest. The user configures the system 10 for volume or three-dimensional imaging, such as selecting an application for volume imaging specific anatomy or inserted device. The user may alter values of one or more presets as desired. Once scanning starts, the system 10 automatically detects the object, scans the object differently than the remaining volume in the field of view, and generates an image or images showing volume of interest. By tracking or detecting the object regularly, the system 10 re-positions the volume of interest for enhanced three-dimensional imaging relative to the volume, providing better image quality for the object of interest automatically.

The system 10 is an ultrasound imager. In one embodiment, the ultrasound imager is a medical diagnostic ultrasound imaging system. In alternative embodiments, the ultrasound imager is a personal computer, workstation, picture archiving and communications system (PACS) station, or other arrangement at a same location or distributed over a network for real-time or post acquisition imaging.

The system 10 implements the method of FIG. 1, the method of FIG. 3, or other methods. The system 10 includes a transmit beamformer 12, a transducer (XDCR) 14, a receive beamformer 16, an image processor 18, a renderer 21, a display 22, a beamformer controller (Bf Controller) 24, and a memory 26. Additional, different or fewer components may be provided. For example, a spatial filter, a scan converter, a mapping processor for setting dynamic range, and/or an amplifier for application of gain are provided. As another example, a user input is provided.

The transmit beamformer 12 is an ultrasound transmitter, memory, pulser, analog circuit, digital circuit, or combinations thereof. The transmit beamformer 12 is configured to generate waveforms for a plurality of channels with different or relative amplitudes, delays, and/or phasing to focus a resulting beam at one or more depths. The waveforms are generated and applied to a transducer array with any timing or pulse repetition frequency. For example, the transmit beamformer 12 generates a sequence of pulses for different lateral and/or range regions. The pulses have a center frequency.

The transmit beamformer 12 connects with the transducer 14, such as through a transmit/receive switch. Upon transmission of acoustic waves from the transducer 14 in response to the generated waves, one or more beams are formed during a given transmit event. The beams are for B-mode or other mode of imaging. Sector, Vector®, linear, or other scan formats may be used. The same region is scanned multiple times for generating a sequence of images. The formed beams have an aperture, origin on the transducer 14, and angle relative to the transducer 14. The beams in the field of view have a desired line density and format.

The transducer 14 is a 1-, 1.25-, 1.5-, 1.75- or 2-dimensional array of piezoelectric (PZT) or capacitive membrane elements. The transducer 14 includes a plurality of elements for transducing between acoustic and electrical energies. For example, the transducer 14 is a one-dimensional PZT array with about 64-256 elements in a wobbler array for mechanical movement of the one-dimensional array to scan a volume. In one embodiment, the transducer 14 is a multi-dimensional array or other array for scanning a volume. For example, the transducer 14 is a transesophageal echocardiography (TEE) array, a volume intercardiac echocardiography (ICE) array, or a trans-thoracic echo (TTE) array.

The transducer 14 is releasably connectable with the transmit beamformer 12 for converting electrical waveforms into acoustic waveforms, and with the receive beamformer 16 for converting acoustic echoes into electrical signals. The transducer 14 includes a plug that may be plugged into an imaging system or wirelessly communicates with the imaging system. The transducer 14 transmits the transmit beams where the waveforms have a frequency and are focused at a tissue region or location of interest in the patient. The acoustic waveforms are generated in response to applying the electrical waveforms to the transducer elements. The transducer 14 transmits acoustic energy and receives echoes. The receive signals are generated in response to ultrasound energy (echoes) impinging on the elements of the transducer 14.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission for detection. Dynamic focusing on receive may be provided. The receive beamformer 16 outputs data representing spatial locations using the received acoustic signals. Relative delays and/or phasing and summation of signals from different elements provide beamformation. In alternative embodiments, the receive beamformer 16 is a processor for generating samples using Fourier or other transforms. The sampling density by the receive beamformer 16 is for a range of depths. Timing is used to select the range of depths over which the sampling occurs. The receive beams have a desired scan line density at an orientation or orientations using an aperture.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental, or other band. The fundamental frequency band may alternatively be used.

The receive beamformer 16 outputs beam summed data representing spatial locations. Data for locations for a volume and/or volume of interest are output.

The beamformer controller 24 and/or another processor configure the beamformers 12, 16. The beamformer controller 24 is a processor, application specific integrated circuit, field programmable gate array, digital circuit, analogy circuit, memory, buffer, combinations thereof, or other device for configuring the transmit and receive beamformers 12, 16.

The beamformer controller 24 may use the memory 26 to acquire and/or buffer values for different beamformer parameters. The values may be accessed by the beamformers 12, 16 and/or loaded from the memory 26 into buffers or memories of the beamformers 12, 16 to configure the beamformers 12, 16. By loading values into registers or a table used for operation, the values of acquisition parameters used by the beamformers 12, 16 for three-dimensional imaging are set. Any control structure or format may be used to establish the imaging sequence. The beamformers 12, 16 are caused to acquire data for three-dimensional imaging at a frame rate, with a transmit focus, at an imaging frequency band, over a depth, with a line density, at a sample density, and/or with a line orientation. Different values of one or more acquisition or scanning parameters may result in a different frame rate, signal-to-noise ratio, penetration, contrast, and/or resolution.

The beamformer controller 24 causes the beamformers 12, 16 to scan a volume of a patient. Any three-dimensional scan format may be used. Similarly, the beamformer controller 24 causes the beamformers 12, 16 to scan a volume of interest within the volume. Any three-dimensional scan format may be used to scan the volume of interest.

The volume of interest scan is separate from and/or acquires additional data not acquired for the rest of the volume. For example, the volume of interest is scanned with scan lines at a different angle or angles than the rest of the volume. The angle relative to the tissue and/or the transducer is different. The volume and volume of interest are scanned at different orientations. Other parameters may be set to scan the volume of interest at a greater resolution, contrast, and/or frame rate as compared to the rest of the volume, such as setting sample density and/or line density differently.

The image processor 18 detects, such as detecting intensity, from the beamformed samples. Any detection may be used, such as B-mode and/or color flow detection. In one embodiment, a B-mode detector is a general processor, application specific integrated circuit, or field programmable gate array. Log compression may be provided by the B-mode detector so that the dynamic range of the B-mode data corresponds to the dynamic range of the display. The image processor 18 may or may not include a scan converter.

The renderer 21 is a graphics processing unit, graphics card, separate computer, processor, or other device for three-dimensional rendering. The renderer 21 is configured by software, hardware, and/or firmware to generate an image or images of the patient from the volume and/or volume of interest data. Separate images for the volume and volume of interest may be generated, such as full volume images until the object is detected and then just volume of interest images thereafter or until the user indicates completion. Alternatively or additionally, an image is generated to represent both the volume and the volume of interest in a single representation. The volume and volume of interest data may be separately processed (e.g., mapped to color or intensity) and then combined for rendering. Alternatively, the volume and volume of interest data are separately rendered and then the resulting rendered data is combined into the image. A sequence of such images may be generated.

In one embodiment, the renderer 21 is configured to generate images only of the volume of interest from scans by the transmit and receive beamformers 12, 16 over a period, such as for four, ten, or more frames. Within an acquisition cycle, the volume of interest is imaged while the full volume is not. Alternatively, the most recent full volume image persists while the volume of interest images are updated. The initial acquisition cycle may include an image or images of the full volume for before transition to imaging the volume of interest. Subsequent repetitions of the acquisition cycle scan the full volume to detect the current location of the anatomy, but a corresponding full volume image is not rendered. Alternatively, a full volume image is rendered when data is available. The images of the full volume are interleaved with images of the volume of interest, but the frame rate of the volume of interest is at least two times the frame rate of the full volume. Other ratios may be provided.

The display 20 is a cathode-ray tube (CRT), liquid crystal display (LCD), monitor, plasma, projector, printer or other device for displaying an image or sequence of images. Any now known or later developed display 20 may be used. The display 20 displays three-dimensional representations. The display 20 displays one or more images representing the volume of interest.

The spatial resolution and/or image quality is based, in part, on the acquisition or scan parameters. The ultrasound imager using different acquisition parameters may result in different spatial resolutions, temporal resolution, or image quality for the displayed image. The volume of interest is smaller than the full volume, so may have a greater image quality than the full volume. The volume of interest may shift in location due to tracking, allowing the user to continue to view the object of interest with higher quality compared to imaging the full volume.

The beamformer controller 24, image processor 18, renderer 21, or other processor is configured to detect the object. Software, hardware, and/or firmware configure for detection of the object. An anatomic structure or inserted device within the patient is automatically identified. A classifier, such as a machine-learnt classifier, is applied to the scan data received from the receive beamformer 16 and representing the full volume. The classifier autonomously detects the position of the object in the volume and/or a bounding box relative to the volume and object.

The detection is repeated over time to track the position of the object at different times. The processor repeats the identification from later acquired ultrasound data from a later full volume scan. The position of the anatomy at a future time may be predicted from past detection and/or modeling of motion of the anatomy. The beamformer controller 24 is configured to cause the transmit and receive beamformers 12, 16 to track a location of the anatomy over time of the volume of interest within the volume based on a position over time of the detected object or bounding box.

The processor (e.g., beamformer controller 24, image processor 18, renderer 21, combination thereof, or other processor) is configured to adjust the scan parameters to scan the volume of interest. The processor may be a GPU (graphics processing unit) and/or a CPU (central processing unit). Only the volume of interest is scanned for most, 75%, 90%, or other amount of time. The full volume may be periodically scanned for tracking, but the remainder of the time just the volume of interest is scanned. The scan parameters are set or adjusted for scanning the volume of interest. The scan line density, sample density, sample rate, depth, lateral extent, scan format, frequency, transmit focus, transmit power, and/or other scan parameters have values assigned to scan the volume of interest and not the rest of the full volume. The scan parameters are adjusted to scan a fan or other ultrasound scan format shaped region enclosing the bounding box and/or object. For example, the scan parameters are set to values for scanning a scan region sized to minimally or minimally with a margin enclose the bounding box. As the volume of interest changes position, the scan parameters are altered.

The beamformer controller 24, image processor 18, renderer 21, and/or the ultrasound imager operate pursuant to instructions stored in the memory 26 or another memory. The instructions configure the system for performance of the acts of FIG. 1. The instructions configure for operation by being loaded into a controller, by causing loading of a table of values (e.g., elasticity imaging sequence), and/or by being executed. The memory 26 is a non-transitory computer readable storage media. The instructions for implementing the processes, methods and/or techniques discussed herein are provided on the computer-readable storage media or memories, such as a cache, buffer, random access memory (RAM), removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for operation of an ultrasound imaging system for ultrasound imaging of a volume of interest, the ultrasound imaging system comprising: a transmit beamformer; a receive beamformer; a transducer; a processor; a renderer; and a display, wherein the method comprises:

a process for acquiring, with the ultrasound imaging system, data representing a volume of a patient; then     a process for locating, by the processor, a target bounding box surrounding an object of interest and additional anatomy with respect to the data representing the volume of the patient, the target bounding box having a multi-sided shape oriented to the object of interest; then     a process for identifying, by the processor, the volume of interest within the volume as a scan region in a scan format enclosing the target bounding box, the volume of interest being less than the volume represented by the data and having a scan-format-based shape different than the multi-sided shape, the scan-format-based shape fit to enclose the multi-sided shape of the target bounding box as the target bounding box is oriented and the scan-format-based shape being oriented relative to the transducer, the fit comprising minimizing the scan-format-based shape to cover all of the target bounding box or cover all of the target bounding box with a margin about the target bounding box, the minimizing making the scan-format-based shape as small as possible while having the geometry of the scan-format-based shape, wherein the process for identifying the volume of interest comprises a process for identifying the scan-format-based shape of the scan region as a minimization of a three-dimensional fan shape being as small as possible while covering all of the target bounding box, the scan-format-based shape having a different lateral and depth extent than the bounding box due to the differences in the scan-format-based shape and the multi-sided shape of the target bounding box, and the multi-sided shape oriented to the object of interest while the scan-format-based shape is oriented to relative to the transducer;

a process for scanning the scan region in the scan format with the ultrasound imaging system; and     a process for generating, with the renderer, an image from data representing the volume of interest acquired through the scanning process of the volume of interest,     wherein the process for locating the target bounding box comprises a process for applying a machine-learnt classifier, or     wherein the process for scanning the scan region comprises a process for repeating a process for scanning the scan region and a process for not scanning remaining parts of the volume of the patient, at least ten times, or     wherein the method further comprises:

a process for determining, by the processor, that the object of interest is in the volume of the patient, from the data representing the volume of the patient;

a process for presenting, with the display, an option to a user for zooming to the volume of interest; and         a process for performing the process for identifying the volume of interest and the process for scanning the scan region in response to user selection of the option.

2. The method of claim 1, wherein the process for acquiring data representing the volume of the patient is executed prior to the process for scanning the scan region, and ceased while the process for scanning the scan region is repeated a plurality of times.

3. The method of claim 1, wherein the process for acquiring data representing the volume of the patient is executed with a first line density, and wherein the process for scanning the scan region comprises a process executed with a second line density greater than the first line density.

4. The method of claim 1 wherein the process for locating the target bounding box comprises a process for locating the multi-sided shape of the target bounding box as a geometric structure having less than thirteen sides and an outer surface different than the object of interest.

5. The method of claim 1, wherein the process for locating the target bounding box comprises a process for detecting a position, orientation, and size of the multi-sided shape of the target bounding box to encompass the object of interest.

6. The method of claim 1, wherein the process for identifying the volume of interest comprises a process for identifying the scan-format-based shape of the scan region as an ultrasound cone region with boundaries covering the target bounding box in depth, elevation, and azimuth.

7. The method of claim 1, wherein the process for acquiring data representing the volume of the patient, the process for scanning the scan region, and the process for repeating comprise a certain acquisition cycle,
the method further comprising: a process for repeating the acquisition cycle; a process for the repeating of the process for acquiring data representing the volume of the patient; and the process for locating the target bounding box comprises a process for tracking an object of interest in the volume of the patient.

8. The method of claim 1, wherein the process for generating an image comprises a process for generating an image of the volume of interest and a process for not generating images of other parts of the volume of the patient.

9. A system for ultrasound imaging of a volume of interest, the system comprising:
a transmit beamformer;
a receive beamformer;
a transducer connectable with the transmit and receive beamformer;
a processor configured to identify an anatomic structure autonomously from an ultrasonic data set responsive to information from the receive beamformer representing a first region of the patient and configured to adjust scan parameters to scan just the volume of interest as a sub-part of the first region, the volume of interest including the anatomic structure and a bounding box enclosing the anatomic structure, the bounding box having a different shape than the anatomic structure and the volume of interest, the processor configured to minimize the volume of interest to be as small as possible while covering all of (a) the bounding box or (b) a margin of the bounding box, the margin being a distance from an edge of the bounding box, wherein the processor configured to minimize is configured to determine a minimization of a lateral extent of the volume of interest (a) to be as small as possible while covering all of the bounding box or (h) to be as small as possible while covering the margin of the bounding box, the volume of interest of the minimization having a different lateral and depth extent than (a) the bounding box or (b) the hound box with the margin, the different lateral and depth extent being due to the different shape of the bounding box than the volume of interest, and the bounding box oriented to the anatomic structure while the volume of interest is oriented to relative to the transducer;
a renderer configured to generate images only of the volume of interest from scans by the transmit and receive beamformers using the scan parameters; and
a display configured to display the images,
wherein the processor is configured to:
repeat the identification from an additional ultrasonic data set responsive to additional information from the receive beamformer and repeat the adjustment of the scan parameters, or
identify the anatomic structure with a machine-learnt classifier.

10. The system of claim 9, wherein the renderer is configured to generate the images of only the volume of interest interleaved with images of the first region.

11. The system of claim 9, wherein the processor is configured to identify the anatomic structure with the bounding box of the anatomic structure, and wherein the processor is configured to adjust the scan parameters to scan a fan shape region as the volume of interest enclosing the bounding box, the fan shape region being a scan shape sized by the minimization to enclose all of the bounding box minimally or to enclose all of the bounding box and the margin of the bounding box minimally.

* * * * *